United States Patent [19]

Dobson

[11] Patent Number: 5,015,773
[45] Date of Patent: May 14, 1991

[54] REDUCTIVE AMINATION OF HYDROXY-CONTAINING COMPOUNDS

[75] Inventor: Ian D. Dobson, North Humberside, England

[73] Assignee: BP Chemicals Limited, London, Great Britain

[21] Appl. No.: 389,748

[22] Filed: Aug. 4, 1989

[30] Foreign Application Priority Data

Aug. 18, 1988 [GB] United Kingdom ............... 8819663

[51] Int. Cl.$^5$ .................. C07C 209/16; C07C 209/18; C07C 231/12
[52] U.S. Cl. .................................... 564/474; 564/153; 564/159; 564/160; 564/192; 564/197; 564/198; 564/199; 564/215; 564/224; 564/399; 564/401; 564/402; 564/478; 564/479; 564/480
[58] Field of Search ............... 564/399, 401, 402, 474, 564/480, 153, 159, 160, 192, 197, 198, 199, 215, 224, 478, 479

[56] References Cited

U.S. PATENT DOCUMENTS

| | | | |
|---|---|---|---|
| 2,953,601 | 9/1960 | Whitaker | 260/585 |
| 3,838,076 | 9/1972 | Moss et al. | 260/2.5 AQ |
| 3,847,992 | 11/1974 | Hotchkiss | 260/584 B |
| 4,036,883 | 7/1977 | Voges et al. | 260/585 B |
| 4,123,462 | 10/1978 | Best | 260/585 B |
| 4,138,437 | 2/1979 | Strauss et al. | 260/583 R |
| 4,152,353 | 5/1979 | Habermann | 260/585 B |
| 4,181,682 | 1/1980 | Watts et al. | 260/584 B |
| 4,207,263 | 6/1980 | Hoffmann et al. | 260/583 R |
| 4,612,335 | 9/1986 | Cuscurida et al. | 521/167 |
| 4,625,063 | 11/1986 | Yokota et al. | 564/480 |
| 4,792,622 | 12/1988 | Yokota et al. | 564/398 |
| 4,888,425 | 12/1989 | Herdle | 544/402 |

FOREIGN PATENT DOCUMENTS

| | | |
|---|---|---|
| 0645984 | 7/1962 | Canada . |
| 0146508 | 6/1985 | European Pat. Off. . |
| 0163253 | 12/1985 | European Pat. Off. . |
| 0197611 | 10/1986 | European Pat. Off. . |
| 0211630 | 2/1987 | European Pat. Off. . |
| 0284398 | 9/1988 | European Pat. Off. . |
| 2057001 | 9/1972 | Fed. Rep. of Germany . |
| 8806579 | 9/1988 | PCT Int'l Appl. . |
| 0163626 | 8/1964 | U.S.S.R. . |
| 0164294 | 8/1964 | U.S.S.R. . |
| 0164295 | 8/1964 | U.S.S.R. . |
| 0166036 | 11/1964 | U.S.S.R. . |
| 0168711 | 2/1965 | U.S.S.R. . |
| 0150521 | 8/1965 | U.S.S.R. . |
| 1341871 | 12/1973 | United Kingdom . |
| 2059792 | 9/1980 | United Kingdom . |
| 2175910 | 12/1986 | United Kingdom . |

*Primary Examiner*—Richard L. Raymond
*Assistant Examiner*—P. O'Sullivan
*Attorney, Agent, or Firm*—Brooks Haidt Haffner & Delahunty

[57] ABSTRACT

An amine is produced by reacting in the presence of hydrogen at elevated temperature a first reactant which is a compound substantially involatile at the elevated temperature employed and having either one, two or more hydroxyl functions, each of which is independently either a primary or secondary hydroxyl function, with a second reactant which is either ammonia or a primary or a secondary amine in the presence of a reductive amination catalyst wherein the reaction is effected in either a continuously or periodically open system.

15 Claims, No Drawings

REDUCTIVE AMINATION OF HYDROXY-CONTAINING COMPOUNDS

The present invention relates in general to the reductive amination of hydroxy-containing compounds, and in particular to the reductive amination of polyether polyols to produce high molecular weight amines.

The catalytic reductive amination of lower molecular weight alkylene oxides, hydroxy-containing compounds, aldehydes and ketones by reaction with ammonia, primary or secondary amines, optionally in the presence of hydrogen gas, is well-known. Representative of the art may be mentioned our copending European application publication No. 0284398 (BP Case No. 6586) which discloses a process for the production of an amine by reacting at elevated temperature a first reactant which is either an alcohol, an aldehyde or a ketone with a second reactant which is either ammonia, a primary or a secondary amine or a nitrile in the presence as catalyst of a composition comprising (i) nickel, (ii) ruthenium, and (iii) at least one other transition metal selected from either the second or third row transition metals. Alcohols which are useful in the aforesaid process are alkanols containing no more than 30 carbon atoms, alkoxypolyethylene glycols containing no more than 30 carbon atoms and diols or polyols and their ether and polyether derivatives, provided that the total number of carbon atoms does not exceed 30 in the case of a primary alcohol.

Amines, and particularly the higher molecular weight amines, are useful in the manufacture of polyurethanes by reaction with isocyanates and epoxy coatings by reaction with epoxides. However, the direct formation of the higher molecular weight amines by reductive amination has hitherto been impossible to achieve in the case of the high molecular weight polyether alcohols having one, two or more hydroxy functions at least one of which is a primary hydroxyl group or only achievable under forcing reaction conditions, for example pressures greater than 750 psig, for other higher molecular weight alcohols. Representative of the art relating to the high pressure process may be mentioned in U.S. Pat. Nos. 3,838,076, 4,181,682, 3,847,992, 4,612,335 and 4,618,717.

In particular, U.S. Pat. No. 4,181,682 claims a polymer composition comprising a polymeric amine having the following structural formula:

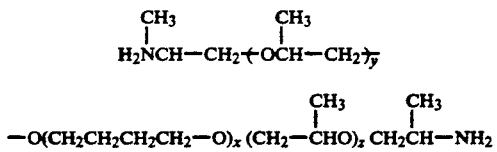

where x is an average number ranging from about 6 to 50, and y and z are average numbers ranging from about 1 to about 20 with the sum of y and z being from 6 to about 40. The disclosure at column 2, lines 38 to 47, reads as follows:

"It is interesting to note that one cannot directly aminate the polybutanediol by means of conventional reductive amination catalysts such as nickel-based catalyst. It was discovered here that when such direct reductive amination is carried out hydrogenolysis occurred. Thus, in order to avoid such hydrogenolysis it was found that the primary alcohol must be transformed into a secondary alcohol by means of the propylene oxide reaction to make the resultant diol amenable to reductive amination".

Thus, it was found impossible in U.S. Pat. No. 4,181,682 to reductively aminate the primary hydroxyl function directly. Other patent publications, for example U.S. Pat. No. 3,838,076, imply that primary hydroxyl functions cannot be reductively aminated.

In all the aforesaid prior art closed reaction vessels were employed.

It has now been found that not only can the reductive amination of hydroxyl-containing compounds be achieved at atmospheric pressure, but also the reductive amination of higher molecular weight compounds containing primary hydroxyl functions can be performed, if a continuously "open" or periodically "open" system is used.

Accordingly, the present invention provides a process for the production of an amine by reacting in the presence of hydrogen at elevated temperature a first reactant which is a compound substantially involatile at the elevated temperature employed and having either one, two or more hydroxyl functions, each of which is independently either a primary or secondary hydroxyl function, with a second reactant which is either ammonia or a primary or a secondary amine in the presence of a reductive amination catalyst wherein the reaction is effected in either a continuously or periodically open system.

In a preferred embodiment of the present invention hydrogen and the second reactant in the gaseous phase are contacted at elevated temperature either continuously or intermittently with the first reactant in the liquid phase, optionally in the presence of a solvent, and a reductive amination catalyst to form a product comprising an amine, water and unreacted gas, and from the product there is removed either continuously or intermittently water and unreacted gas.

It is preferred to contact hydrogen and the second reactant continuously with the first reactant and catalyst and to continously remove water and unreacted gas.

The water and unreacted gas removed from the product may be separated either wholly or partially, suitably by condensing the water, and the unreacted gas so-separated may be recycled to the reaction.

The process can be operated at atmospheric pressure which may provide advantages in terms of lower capital expenditure and operating costs, when compared with the prior art elevated pressure processes.

Another unexpected important advantage of operating according to the invention is that improved selectivities to desirable products can be achieved. During reductive aminations at pressure in sealed systems using a primary amine as the aminating agent, it is our experience that a selectivity loss occurs. This may be demonstrated by reference to the reaction of a polyether polyol with a primary amine as the aminating species in which the following reactions are believed to occur:

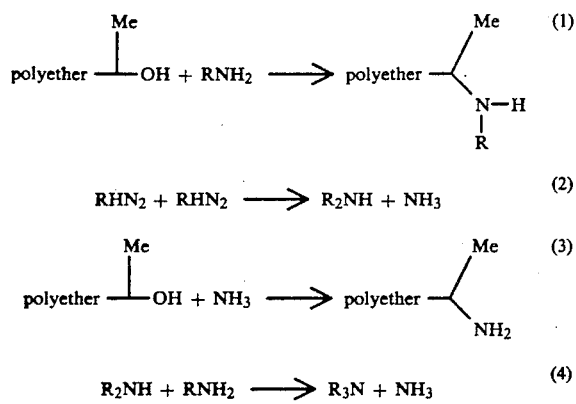

$$RHN_2 + RHN_2 \longrightarrow R_2NH + NH_3 \quad (2)$$

$$R_2NH + RNH_2 \longrightarrow R_3N + NH_3 \quad (4)$$

Reaction (1) is the reaction desired. The self-condensation reactions (2) and (4) not only waste amine but also, more importantly, lead to reaction (3) which produces an unwanted by-product not readily separable from the desired secondary amine terminated polyether. In the open system according to the present invention, this selectivity loss is substantially eliminated. It is presumed that the self-condensation still occurs but because its products are continuously or intermittently removed these remain present at only very low levels in the reactor. The primary amine which is continuously or intermittently fed into the polyether polyol remains throughout in high concentration and consequently is by far the dominant aminating species. It is therefore a major advantage (of using a system in which the ammonia is removed) to be able to produce in essentially pure form a polyether polyol functionalised with a secondary amine group.

The first reactant is a compound substantially involatile at the elevated temperature employed and having either one, two or more hydroxyl functions, each of which is independently either a primary or secondary hydroxyl function. Subject to the proviso that it must be involatile at the reaction temperature the compound may be a monohydric alcohol, suitably an alkanol of the formula:

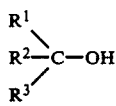

wherein
$R^1$ is hydrogen, and
$R^2$ and $R^3$ are either aliphatic alkyl groups or substituted aliphatic alkyl groups.

The groups $R^2$ and $R^3$ may be substituted, for example, with amide, amine or ether groups.

Alternatively, subject to the same proviso, the compound may be a dihydric alcohol, suitably a diol, for example ethylene glycol, propylene glycol, butylene glycol, alkylene glycols, polyalkylene glycols, mixed polyalkylene glycols and their ether and polyether derivatives.

Alternatively, the compound may be a polyhydric alcohol, suitably a polyhydric alcohol having more than two hydroxyl groups, each being attached to a substituted carbon atom. Suitable examples of polyhydric alcohols include glycerol and triethanolamine.

A preferred class of compound is the polyether alcohols, including polyether monools, polyether diols and polyether polyols. Generally, these are high molecular weight materials, typical molecular weights being in the range from about 200 to 10,000. It is an advantage of the invention that polyether amines can be derived from polyether alcohols having primary hydroxyl functions.

As the second reactant there may be used either ammonia or a primary or secondary amine. The amine may be either an aliphatic or an aromatic amine. Suitably the amine may be a primary aliphatic amine. The amine may suitably contain from 1 to 30 carbon atoms.

Hydrogen of commercial purity may be used, with or without further purification.

As catalyst there may be used any reductive amination catalyst, Nickel-containing catalysts are preferred. Powdered elemental nickel, Raney nickel and supported nickel, for example nickel supported on gamma-alumina, may all be used as catalysts.

A preferred catalyst is a composition comprising (i) nickel, (ii) ruthenium, and (iii) at least one other transition metal selected from either the second or third row transition metals.

As regards the catalyst composition, any transition metal other than ruthenium may be used as component (iii). In the context of this specification the term 'transition metal' is defined as a metal having a partially filled 4d or 5d shell in at least one of its oxidation states. Suitable transition metals include palladium, rhenium and iridium, either individually or in combination.

Preferably, the catalyst composition is supported on a suitable support. Suitable supports include aluminas, silicas, silica-aluminas and carbons. A preferred support is gamma-alumina. Zeolites may also be used as supports.

As regards the relative proportions of components (i), (ii) and (iii) in the catalyst composition, the major component will generally be component (i), i.e. nickel, and components (ii), i.e. ruthenium, and (iii) i.e. transition metal(s) will be minor components. Thus, nickel may suitably form from 50 to 95% by weight of the catalyst composition and together ruthenium and transition metal may form the remainder of the composition. Typically the supported catalyst composition may contain about 10% nickel and 1% each of ruthenium and transition metal(s), the remainder of the composition being the support. However, higher nickel loadings may be used if desired.

The catalyst composition may be prepared by any of the methods conventionally employed for the production of catalysts, for example by precipitation or by impregnation. The supported composition is suitably prepared by an impregnation technique, which may be by co-impregnation or by sequential impregnation, preferably the latter. Impregnation techniques are well-known in the art and include both the incipient wetness technique and the excess solution technique.

A preferred process for producing a catalyst composition for use in the process of the present invention comprises the steps of (A) impregnating a support with a solution of a compound of nickel, (B) calcining the nickel compound present in the impregnated support obtained in step (A), (C) impregnating the impregnated support obtained in step (B) with a solution of a compound of a transition metal selected from either the second or third row transition metals, (D) impregnating the impregnated support obtained in step (C) with a solution of a compound of ruthenium, and (E) activating the composition obtained in step (D).

Optionally, after step (C), the catalyst may be contacted with either hydrogen or air at elevated temperature. The elevated temperature may suitably be in the range from 250° to 500° C., preferably from 250° to 350° C., for contact with hydrogen and from 500° to 600° C. for contact with air.

Suitable compounds of the metals include salts of the metals, for example the nitrates, halides and carboxylates. The compounds of the metals are used in the form of solutions thereof. Any suitable solvent may be employed for this purpose. A convenient solvent is water, though other solvents, such as for example alcohols, may be employed.

In step (B) of the process for producing the catalyst the compound of nickel present in the impregnated support obtained in step (A) is calcined. Calcination may suitably be accomplished at a temperature in the range from 550° to 600° C., typically about 580° C., though lower temperatures may be employed.

Activation (step E) may suitably be accomplished by heating the composition at elevated temperature, suitably greater than 280° C. in the presence of a reducing gas, for example hydrogen, for a period sufficient to activate the catalyst, typically for at least 3 hours and thereafter allowing the catalyst to cool in the presence of an inert gas, for example nitrogen. The activation step (step E) may be carried out as a further step in the preparative method, or may be carried out in the reductive amination reactor immediately prior to operation of the process of the invention, or both.

Further details of this catalyst and its preparation may be found in our copending European application publication No. 0284398 (BP Case No. 6586).

The process may be operated at a temperature in the range from 150° to 350° C., preferably from 180° to 300° C. Atmospheric pressure or slightly above may suitably be employed.

The process may be operated batchwise or continuously. Generally, it will be necessary to separate the catalyst from the liquid product of the reaction. This may suitably be accomplished by filtration or centrifugation.

The process of the invention will now be further illustrated by reference to the following Examples.

EXAMPLE 1

20 g of polyether polyol CP1 having molecular weight around 4800 and with three secondary hydroxyl functions was placed in a 250 ml glass reactor. 3 g of water washed (to pH 7) raney nickel was added to the polyol. The reactor was provided with an ammonia/hydrogen sparge and an outlet leading to a take off condenser. Hydrogen and ammonia in a ratio greater than 3:1 was sparged into the polyol catalyst mixture at atmospheric pressure. The reactor was heated to 200° C. and the sparge continued at this temperature for 6 hours. The sparge was then altered so as to be of hydrogen only and this was continued for a further hour. The reactor was then cooled and the product removed. After separation of the nickel catalyst, amination of over 50% of the hydroxyl functions was indicated by $^{13}$C NMR. The product showed a rapid crosslinking reaction with a diisocyanate typical of a polyether polyamine.

This Example shows that amination can be achieved at atmospheric pressure and 200° C. These conditions, particularly pressure, being significantly milder than the prior art, typically over 50 bar/over 200° C.

EXAMPLE 2

The reaction described in Example 1 was performed using 20 g of polyether polyol type C1634, having molecular weight around 4800 and 3 primary hydroxyl functions. Analysis by $^{13}$C NMR showed over 50% amination of the polyol. Reaction with a diisocyanate gave very rapid crosslinking typical of a polyether polyamine.

In addition to employing the mild conditions exemplified above, this reaction shows that contrary to Texaco patent disclosures, it is possible to aminate a primary hydroxyl functionalised polyether polyol to give a new material of general formula:

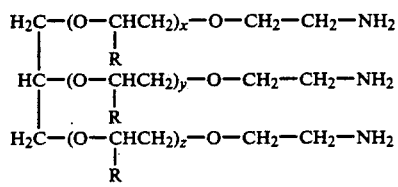

EXAMPLE 3

140 g of polyol CP-1 and 40 g raney nickel were placed in a reactor. Hydrogen was sparged through a 50% w/w solution of propylamine in water and this gas stream fed into the reactor at 190° C./atmospheric pressure for 24 hours. The product recovered was aminated to over 90% conversion with the end group

Amination by ammonia was not evident.

COMPARISON TEST

The test was performed in a sealed system under reaction conditions more typical of the prior art.

4 Kg of polyether polyol CP-1 and 400 g of raney nickel were charged into a 7 dm$^3$ stainless steel autoclave. 200 ml of propylamine was then added and the autoclave was connected to a gas manifold. 240 psig of hydrogen was then pumped into the autoclave which was heated to 220° C. for 16 hours. The product recovered showed by $^{13}$CNMR analysis a conversion of about 20% with 50% selectivity to the propylaminated end group and 50% selectivity to the undesired NH$_2$ end group. Dipropylamine and tripropylamine were observed to be reaction products.

The Test demonstrates the lower selectivity to desired product obtained in a closed system.

This is not an example according to the invention and is included only for the purpose of comparison.

I claim:

1. A process for the production of a primary, secondary or tertiary amine by reacting in the presence of hydrogen at atmospheric pressure and elevated temperature a polyether alcohol as a first reactant which is substantially involatile at the elevated temperature and has at least one hydroxyl function, each of which is independently either a primary or secondary hydroxyl function, with a second reactant which is either ammonia or a primary or a secondary amine in the presence of a reductive amination catalyst wherein the reaction is effected in either a continuously or periodically open system to remove self-condensation by-products of the second reactant.

2. A process according to claim 1 wherein hydrogen and the second reactant in the gaseous phase are contacted at elevated temperature either continuously or intermittently with the first reactant in the liquid phase, optionally in the presence of a solvent, and a reductive amination catalyst to form a product comprising an amine, water and unreacted gas, and from the product there is removed either continuously or intermittently water and unreacted gas.

3. A process according to claim 2 wherein hydrogen and the second reactant are contacted continuously with the first reactant and water and unreacted gas are continuously removed.

4. A process according to claim 1 wherein the first reactant is either a polyether monool, a polyether diol or a polyether polyol having a molecular weight in the range from about 200 to 10,000.

5. A process according to claim 1 wherein the second reactant is ammonia.

6. A process according to claim 1 wherein the second reactant is a primary aliphatic amine containing from 1 to 30 carbon atoms.

7. A process according to claim 1 wherein the catalyst is a nickel-containing catalyst.

8. A process according to claim 7 wherein the catalyst is a composition comprising (i) nickel, (ii) ruthenium, and (iii) at least one other transition metal selected from either the second or third row transition metals.

9. A process according to claim 8 wherein component (iii) of the catalyst composition is palladium, rhenium or iridium either individually or in combination.

10. A process according to claim 7 wherein the catalyst composition is supported on gamma-alumina.

11. A process according to claim 1 wherein the elevated temperature is in the range from 150° to 350° C.

12. A process for the production of a secondary or tertiary amine by reacting in the presence of hydrogen at atmospheric pressure and elevated temperature a polyether alcohol as a first reactant which is substantially involatile at the elevated temperature and has at least one hydroxyl function, each of which is independently either a primary or secondary hydroxyl function, with a second reactant which is either a primary or a secondary amine in the presence of a reductive amination catalyst wherein the reaction is effected in either a continuously or periodically open system to remove self-condensation by-products of the second reactant.

13. A process according to claim 12 wherein the second reactant is a primary aliphatic amine containing from 1 to 30 carbon atoms.

14. A process according to claim 12 wherein the second reactant is a secondary amine.

15. A process according to claim 1 wherein the second reactant is ammonia and the amine produced by the process is a primary amine.

* * * * *

UNITED STATES PATENT AND TRADEMARK OFFICE
CERTIFICATE OF CORRECTION

PATENT NO. : 5,015,773
DATED : May 14, 1991
INVENTOR(S) : IAN D. DOBSON

It is certified that error appears in the above-identified patent and that said Letters Patent is hereby corrected as shown below:

Col. 3, line 9, "$RHN_2 + RHN_2$" should read --$RNH_2 + RNH_2$--

Signed and Sealed this

Twenty-second Day of September, 1992

Attest:

DOUGLAS B. COMER

Attesting Officer

Acting Commissioner of Patents and Trademarks